United States Patent [19]
De Cubber et al.

[11] Patent Number: 6,013,094
[45] Date of Patent: Jan. 11, 2000

[54] METHOD AND DEVICE FOR TREATING SCAR TISSUE

[75] Inventors: Jan Prosper Dennis De Cubber, Zaventem; Eric Andre Maria Van Den Kerckhove, Haverlee; Willy Dennis Boeckx, Linden, all of Belgium

[73] Assignees: Otto Bock Orthopaedische Industrie Besitz- Und Verwaltungskommandit- Gesellschaft, Duderstadt, Germany; K.U. Leuven Research and Development, Leuven, Belgium

[21] Appl. No.: 08/909,059

[22] Filed: Aug. 14, 1997

[30] Foreign Application Priority Data

Aug. 14, 1996 [EP] European Pat. Off. ............ 96202282

[51] Int. Cl.$^7$ ................................... A61B 17/00
[52] U.S. Cl. ....................................... 606/204.15
[58] Field of Search .................. 606/201, 202, 606/204.15

[56] References Cited

U.S. PATENT DOCUMENTS

| | | | |
|---|---|---|---|
| 2,882,892 | 4/1959 | Kosior | 606/204.15 |
| 3,171,410 | 3/1965 | Towle, Jr. et al. | 606/202 |
| 4,193,401 | 3/1980 | Marinello. | |
| 4,202,331 | 5/1980 | Yale. | |
| 4,224,945 | 9/1980 | Cohen. | |
| 4,436,089 | 3/1984 | Schmid. | |
| 5,376,067 | 12/1994 | Daneshvar. | |
| 5,792,174 | 8/1998 | Ioan | 606/204.15 |

FOREIGN PATENT DOCUMENTS

| 0 035 583 | 9/1981 | European Pat. Off.. |
|---|---|---|
| WO 91 18571 | 12/1991 | WIPO. |

*Primary Examiner*—Michael Buiz
*Assistant Examiner*—William W. Lewis
*Attorney, Agent, or Firm*—Foley & Lardner

[57] ABSTRACT

The invention relates to methods for treating scar tissue, wherein the scar tissue is covered with a masking element, and the masking element is pressed onto the scar tissue with an adjustable force by means of a pressure control unit and which is connected with inflatable or suction members in the masking element. The invention also relates to a device for treating scar tissue, consisting of a masking element which contacts the scar tissue, a supporting part which presses the masking element onto the tissue and means for adjusting the force with which the masking element is pressed onto the tissue. In another embodiment, the device is provided such that an active substance can be delivered in a controlled manner to the scar tissue through the inflatable or suction members in the masking element.

7 Claims, 4 Drawing Sheets

METHOD AND DEVICE FOR TREATING SCAR TISSUE

BACKGROUND OF THE INVENTION

The invention relates to a method for treating scar tissue, in which at least one masking element is brought into occlusive contact with the scar tissue. Such a treatment method is generally known and is employed in order to counteract the formation of hypertrophic scar tissue in cases of injuries to the epidermis and dermis caused by burns.

Hypertrophic scars generally occur when the skin is completely damaged, that is to say both the epidermis and also the underlying dermis, for example in cases of second or third degree burns. These scars are not only disfiguring, especially if they are located on highly visible regions of the body, such as the face or neck, but can also lead to physical disabilities if they form in the vicinity of muscles or joints. An example in this context would be a burn injury to the palm of the hand, in which these scars can lead to a permanent contracture of the wrist. Burn scars thus cause the patient physical as well as psychological damage, and the healing process is additionally so lengthy—several months to over a year depending on the degree of the burns—that the costs involved are very great.

For this reason, considerable research work has been devoted to developing treatment methods which as far as possible counteract the formation of hypertrophic scars. There are therefore also a number of variations of the treatment method cited by way of introduction.

Thus, for example, it is known to exert pressure on the scar tissue by means of compression bandages or gauze compressors or by means of individually modeled and shape-stable support casts or splints. It has been found that the duration of healing of a scar can be shortened by means of exerting such pressure. However, this known treatment method has some disadvantages. Thus, the pressure exerted by compression bandages has proven inadequate, whilst shape-stable support casts, which are generally made of hard synthetic material, impede the skin's recovery.

To treat scar tissue of this kind, another method is known in which no pressure is exerted, and instead the tissue is screened off from the surrounding area by applying to it a masking element made of a tissue-compatible and malleable polymer material, preferably silicone. It has been found that masking elements of this kind promote the skin's recovery, probably because this method counteracts fluid loss. However, as no pressure is exerted, it is only partially possible in this way to counteract the formation of hypertrophic scar tissue.

Finally, combinations of these treatment methods are also known in which use is made of masking elements made of silicone which are pressed firmly onto the scar tissue. Although this treatment method does combine the advantages of both said methods, the pressure which is obtained in practice in this way proves not to be optimal, probably because the force with which the scar tissue is pushed back in this method is not sufficient throughout the entire healing process.

In addition to this, all the aforementioned treatment methods have the disadvantage that the scar tissue is masked during treatment and is inaccessible, so that no active substances can be applied thereon, such as medications which might be able to promote the healing process.

SUMMARY OF THE INVENTION

It is therefore one object of the present invention to provide a device which can be used in methods of treating scar tissue, yet avoids the disadvantages of the foregoing treatments.

According this object of the invention, a device is provided for treating scar tissue, which comprises: at least one masking element, to be brought into contact with the scar tissue, which can be made of a tissue-compatible polymer; a supporting part, which holds the masking element on the scar tissue; and pressure-regulating means, located between the supporting part and the masking element, which regulates the force with which the masking element is pressed onto the tissue and which can be operated using a pressure medium.

Further according to this object, a device is provided, wherein the pressure-regulating means and the masking element are integrated, forming an inflatable member or suction member. The pressure-regulating means optionally comprises adjustable pump means connected to the inflatable member or suction member.

According to this same object, a device is provided, comprising a plurality of inflatable members connected to the supporting part and switching means located between the pump means and the inflatable members, for alternately connecting the pump means to each of the inflatable or suction members.

It is another object of the invention to provide a device which can be left in place while underlying scar tissue is treated with an active substance.

According to this object of the invention, a device is provided for treating scar tissue, which comprises means, connected to a masking element, for metered delivery of an active substance to the scar tissue.

According to this same object, a device is provided, wherein the pressure medium comprises an active substance.

It is yet another object of the present invention to provide improved methods for treating scar tissue.

According to this object of the invention, methods for treating scar tissue are provided, which may be implemented using devices such as those of the invention.

One method according to this object provides contacting scar tissue with a masking element using adjustable force.

Another method according to this object provides a cooled pressure medium, which is used to apply adjustable force to scar tissue.

Another method according to this object, involves delivering an active substance in a metered manner to the scar tissue through a masking element of a device, without the need to remove the device.

In yet another method according to this object, an active substance is used as a pressure medium, which is used to apply adjustable force to scar tissue.

DETAILED DESCRIPTION OF THE INVENTION

The aim of the invention is to make available a treatment method in the above sense, but in which the above-described disadvantages are not obtained. According to a first feature of the invention, this is achieved by means of the fact that the force with which the masking element is pressed onto the scar tissue is adjustable. In this way, during the healing process, the pressure can be adapted to the respective counter-pressure being exerted by the scar tissue, with the result that formation of hypertrophic scars can in all situations be prevented or at least delayed.

According to a second feature of the invention, the aforementioned aim is achieved by means of the fact that an active substance can be delivered in a metered manner to the scar tissue through the masking element. In this way, the scar can be treated from outside despite the presence of the masking element.

The invention also relates to a device with which the above-mentioned novel treatment method can be carried out. This device can be provided in conventional manner with at least one masking element to be brought into contact with the scar tissue, and with a supporting part which presses the masking element onto the tissue, and according to a first feature of the invention the device is distinguished by the fact that means are located between the supporting part and the masking element and are used for adjusting the force with which the masking element is pressed onto the tissue.

According to another feature of the invention, a device of this type may be distinguished by the fact that it comprises means which are connected to the masking element and are used for controlled delivery of an active substance to the scar tissue.

Preferred embodiments of the invention are described hereinafter on the basis of an example, with reference being made to the appended figures. Other embodiments will be evident to the skilled artisan.

Figure 1:
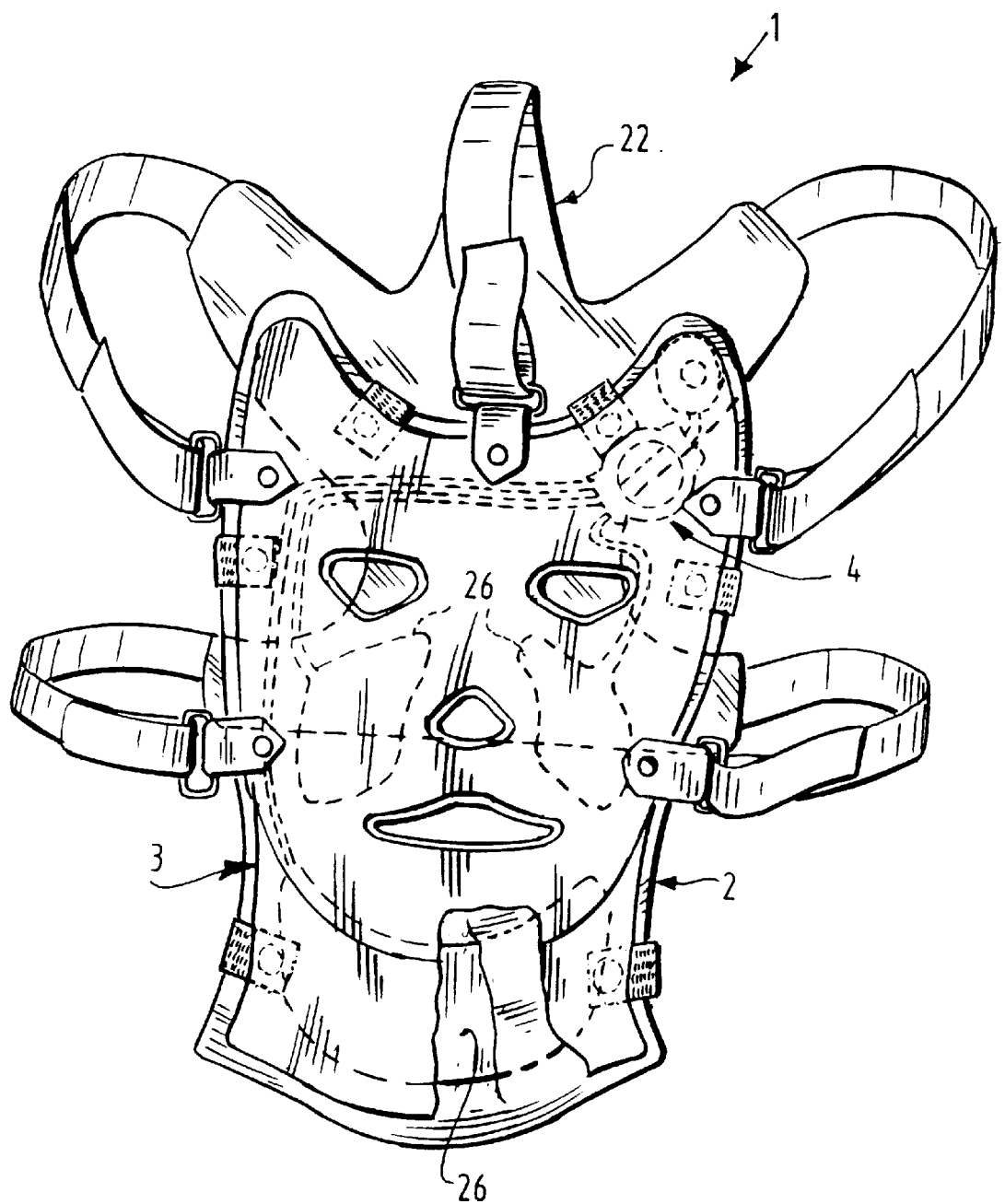
FIG. 1 is a perspective front view of a first embodiment of the device according to the invention.

A device 1 for treating scar tissue consists of a masking element 2 which is to be brought into contact with the scar tissue, and of a supporting part 3 which is connected to the masking element 2 and presses the latter onto the tissue (FIG. 1). The masking element 2 is made of a malleable, tissue-compatible polymer material such as silicone, while the supporting part 3 is made of a shape-stable material such as a hard synthetic material or light metal. The size and shape of the masking element 2 and of the supporting part 3 are adapted to those of the part of the body on which the scar tissue is present, with the masking element 2 projecting slightly beyond the supporting part 3 in order to guarantee a certain degree of comfort of wear.

Figure 5:
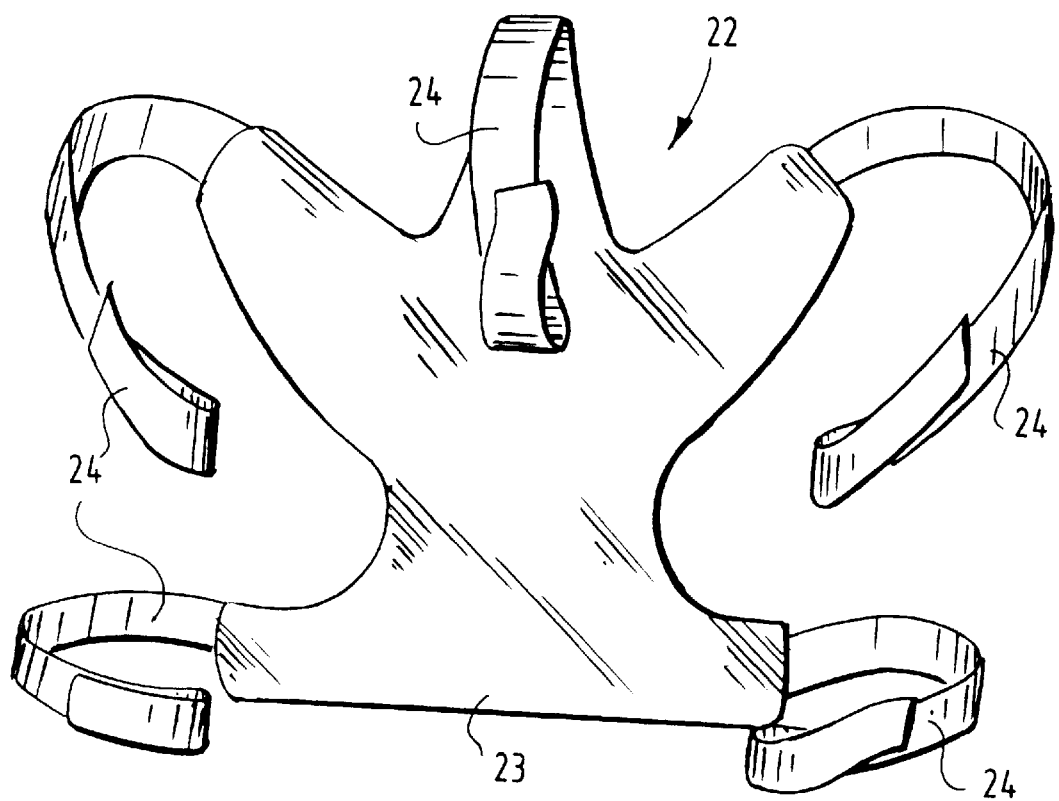
FIG. 5 shows the device for securing the device depicted in FIG. 1.

The device 1, which in the present example corresponds to a mask for treating burns to the face, is thus in principle tailor-made for a specific patient. The device 1 is further provided with means 22 for securing the supporting part 3 and the masking element 2 on the part of the body which is to be treated, in the present case in the form of a head frame with a number of straps 24 to be applied around the patient's head, and with a pressure compensation plate 23 which connects these straps 24 (FIG. 5). In a first embodiment of the invention, means 4 are further provided between the supporting part 3 and the masking element 2 and are used for adjusting the force with which the masking element 2 is pressed onto the tissue, which pressure-regulating means 4 are incorporated in the masking element 2.

Figure 2:
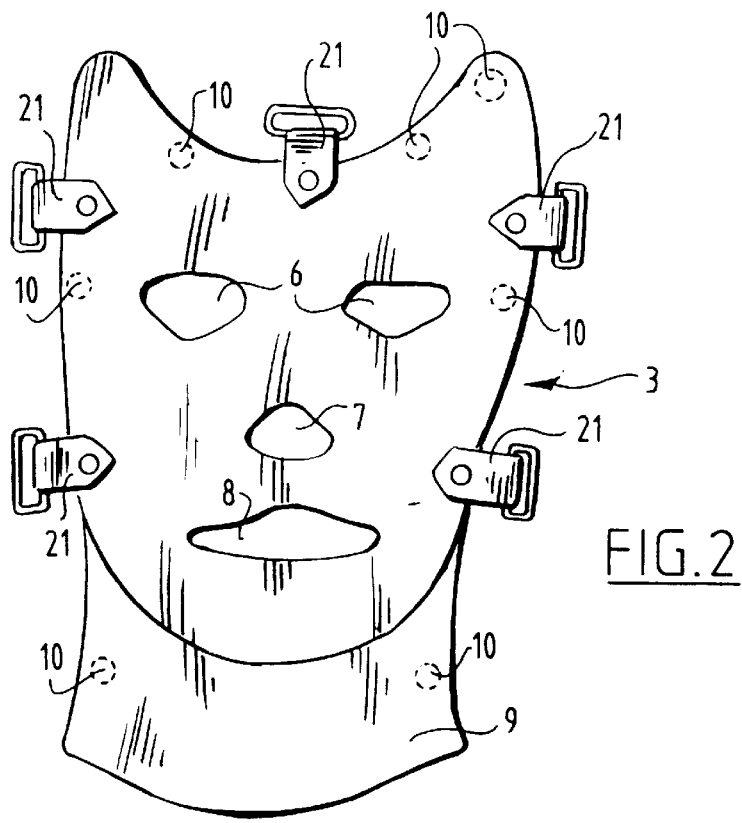
FIG. 2 is a front view of the supporting part of the device depicted in FIG. 1.

In the present example, the supporting part 3 (FIG. 2) consists of a part 5 which covers the face, and of a neck part 9 which is connected to the face part 5. The latter has openings 6, 7 and 8 for the patient's eyes, nose and mouth, respectively. The supporting part also has means 10 for connecting it to the masking element 2, in the present case in the form of small Velcro parts. Finally, the edge of the supporting part 3 has securing straps 21 for securing it to the bead frame 22.

Figure 3:
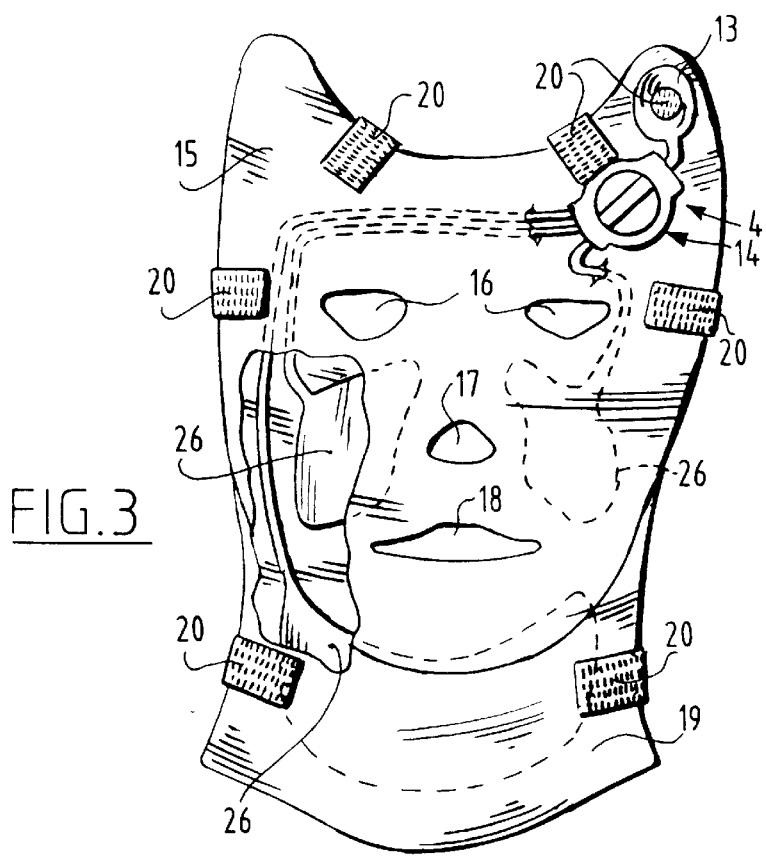
FIG. 3 is a front view of the masking element of the device depicted in FIG. 1.

The masking element 2 (FIG. 3), which, as has been mentioned, largely corresponds in terms of shape and size to the supporting part 3, likewise consists of a face part 15 and a neck part 19. The face part 15 once again has openings 16, 17 and 18 for the eyes, nose and mouth. The masking element 2 also has connection means 20, again in the form of small Velcro parts, which cooperate with the connection means 10 of the supporting part 3.

The masking element 2 is additionally provided with the means 4 for adjusting the pressure force thereof. The pressure-regulating means are pneumatic in the present example and are therefore operated by a gaseous pressure medium, in the present case simply air. However, it would also be possible for these means to be hydraulic means, in which case they would then be operated by a fluid pressure medium. The fluid pressure medium could in this case advantageously be cooled, which would additionally alleviate the pain caused by the wounds. Completely different means of adjusting the pressure force, for example mechanical means, are also conceivable in this context.

The pressure-regulating means 4 consist of a number of inflatable members 26 which are each located between the supporting part 3 and the masking element 2, as a result of which the masking element 2 is pressed firmly locally onto the near tissue. In the present example, the inflatable members 26 are incorporated in the masking element 2, and they consist of a number of cavities arranged in the masking element 2 and of tubings 12 connected to these cavities. Thus, the pressure-regulating means and the masking element may be integrated to form at least one inflatable member. The precise location of these inflatable members 26 will of course depend upon where exactly the scars to be treated are situated, and this location will therefore vary from one masking element 2 to the next.

Figure 4:
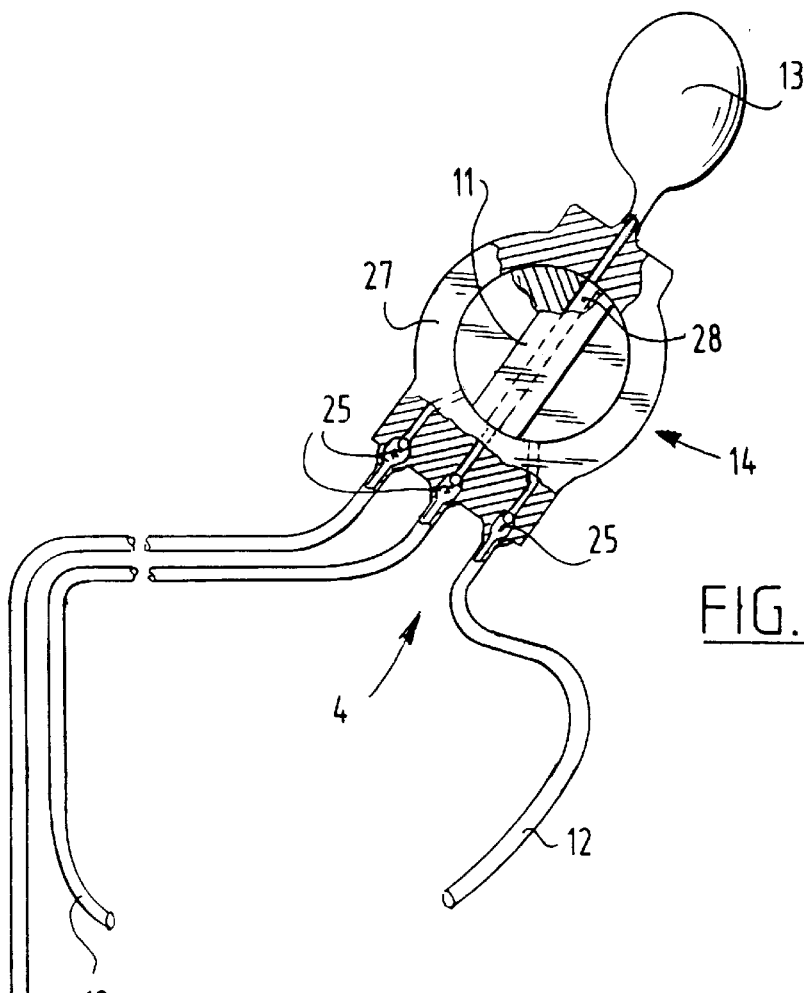
FIG. 4 shows the pressure-regulating device of the device depicted din FIG. 1.

The inflatable members 26 are connected to adjustable pump means 13, in the present example in the form of a simple hand pump, via non-return valves 25 (FIG. 4) which prevent the pressure in the members 26 from dropping. Although a pump 13 could of course in principle be connected to each member 26, the present example has switching means 14 between the members 26 and the single pump 13, so that the pump 13 can be connected alternately to each of the inflatable members 26. In the present example, these switching means 14 consist of a three-way valve with a valve body 27 in which a switch 11, located therein and with integrated connection tubing 28, can be set to three positions, in which case the pump 13 is then connected to one of the tubings 12, which in each case lead to one of the inflatable members 26.

In this way, the pressure in each of the inflatable members 26 can be precisely adjusted as a function of the counter-pressure of the underlying tissue. As to how high the pressure should be in each case, opinions are still divided, the general assumption being that this pressure should at any rate be higher than the capillary pressure in the scar tissue in order to delay or even prevent the formation of collagen fibers and to effect a parallel layering of these fibers in order in this way to prevent pulling. Fluctuations in counter-pressure, which may occur during the healing process, can in any event be compensated, so that as a result the pressure has an optimum value under all circumstances. This promotes healing. It is estimated that the healing process can even be shortened by about 30 percent in this way, and this, together with the advantages for the patient's well-being, also of course results in substantial cost savings. In addition, this shorter healing time is not merely a result of the pressure being optimum under all circumstances; there is also the fact that the adjustment of the pressure also achieves an optimum fit of the masking element, as this is pressed in a uniform manner onto the damaged part of the body. This leads to greater comfort of wear and to optimum contact between the material of the masking element and the wound.

Figure 6:
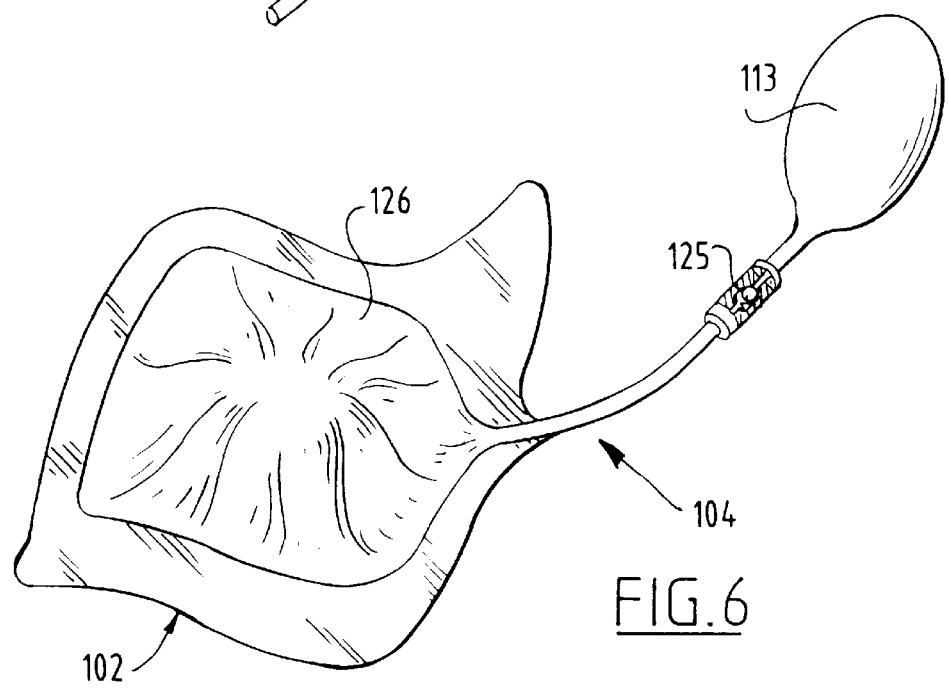
FIG. 6 shows another embodiment of the device according to the invention.

The above-described embodiment of the device according to the invention is especially suitable for treating extensive scars, as often occur in the case of burns to the skin of the face. In another embodiment for treating less extensive scarring (FIG. 6), the masking element 102 forms, together with an inflatable member 126, a pressure pad which is connected to a hand pump 113 via a line 112 and a non-return valve 125. This pressure pad can, for example, be fixed to the scar tissue to be treated by means of a support cast (not shown), for example a splint or compression bandage.

According to a second feature of the invention, both the aforementioned embodiments of the device can be designed in a simple manner such that an active substance can be delivered in a metered manner to the scar tissue through the masking element 2. To this end, the masking element must be permeable to active substances, which can be achieved by using a selectively permeable material for the masking element. An active substance is an substance which is therapeutically or cosmetically effective in treating scar tissue or preventing scarring.

To deliver the active substance to the masking element, it is possible to use the same devices as are used for adjusting the pressure force. For this purpose, the pump means 13, 113 can be replaced by an active substance container. The active substance can in this way flow through the tubings 12, 112 to the members 26, 126, where the active substance then gradually passes through the masking element 2 and is taken up by the scar tissue. The scar tissue can be treated in this way and yet remain screened off from the surrounding air, as a result of which the healing process is also substantially shortened.

Of course, it is also possible to combine both aspects of the invention by designing the device in such a way that the active substance is used as pressure medium, and consequently a constantly adjustable pressure of the active substance is achieved. It is assumed that the healing of scar tissue can be substantially promoted by such a combination of treatment methods, which combination unites all the aforementioned advantages, which increases the patient's well-being and will also lead both directly and indirectly to cost savings to the health services.

Although the invention has been described above on the basis of a number of specific illustrative embodiments, it should be noted that it is of course not limited to these.

European Application Number 96202282.8, filed Aug. 14, 1996, is hereby incorporated by reference in its entirety.

What is claim is:

1. A device for treating scar tissue, comprising:
   (a) at least one masking element, to be brought into contact with the scar tissue;
   (b) a supporting part, which holds said masking element onto the scar tissue; and
   (c) pressure-regulating means that is operated using a pressure medium, located between said supporting part and said masking element, which regulates the force with which said masking element is pressed onto the tissue, wherein said pressure-regulating means and said masking element are integrated, forming an inflatable member, with the masking element forming the side of the device facing the scar tissue, wherein said pressure-regulating means comprise adjustable pump means which are connected to said inflatable member, and further wherein a plurality of inflatable members are connected to said supporting part; and there is also included switching means, located between said pump means and said inflatable members, for alternately connecting said pump means to each of said inflatable members.

2. A device for treating scar tissue, comprising:
   (a) at least one masking element, to be brought into contact with the scar tissue;
   (b) a supporting part, which holds said masking element onto the scar tissue;
   (c) pressure-regulating means that is operated using a pressure medium, located between said supporting part and said masking element, which regulates the force with which said masking element is pressed onto the tissue; and, further comprising means, connected to said masking element, for metered delivery of an active substance to the scar tissue.

3. The device according to claim 2, wherein said metering means comprise an active substance container connected to said masking element, and said masking element is permeable to said active substance.

4. The device according to claim 3, wherein said pressure medium comprises said active substance.

5. A method for treating scar tissue, comprising bringing at least one masking element into occlusive contact with the scar tissue, wherein the masking element is pressed onto the scar tissue with an adjustable force, wherein said force is adjusted by applying pressure to the masking element, on the side opposite from the scar tissue, using a pressure medium, wherein said pressure medium can be cooled.

6. A method for treating scar tissue, comprising bringing at least one masking element into occlusive contact with the scar tissue, wherein the masking element is pressed onto the scar tissue with an adjustable force, further comprising delivering an active substance in a controlled manner to the scar tissue through the masking element.

7. The method according to claim 6, wherein said active substance is used as pressure medium.

* * * * *